(12) United States Patent
Silver

(10) Patent No.: US 12,324,724 B2
(45) Date of Patent: Jun. 10, 2025

(54) FORWARD OSMOSIS MEDICAL AND WOUND CARE DEVICES

(71) Applicant: Brian H. Silver, Glenview, IL (US)

(72) Inventor: Brian H. Silver, Glenview, IL (US)

(*) Notice: Subject to any disclaimer, the term of this patent is extended or adjusted under 35 U.S.C. 154(b) by 883 days.

(21) Appl. No.: 17/430,169

(22) PCT Filed: Feb. 10, 2020

(86) PCT No.: PCT/US2020/017558
§ 371 (c)(1),
(2) Date: Aug. 11, 2021

(87) PCT Pub. No.: WO2020/167694
PCT Pub. Date: Aug. 20, 2020

(65) Prior Publication Data
US 2022/0151835 A1   May 19, 2022

Related U.S. Application Data

(60) Provisional application No. 62/805,470, filed on Feb. 14, 2019, provisional application No. 62/804,759, filed on Feb. 13, 2019.

(51) Int. Cl.
*A61F 13/00* (2024.01)
*A61F 13/0203* (2024.01)
(Continued)

(52) U.S. Cl.
CPC .... *A61F 13/00063* (2013.01); *A61F 13/0206* (2013.01); *A61F 13/0213* (2013.01);
(Continued)

(58) Field of Classification Search
CPC ............ A61F 13/00063; A61F 13/0206; A61F 13/0213; A61F 13/0223; A61F 13/05;
(Continued)

(56) References Cited

U.S. PATENT DOCUMENTS 4,671,267 A   6/1987   Stout
8,439,894 B1  5/2013   Miller
(Continued)

FOREIGN PATENT DOCUMENTS

WO   WO-2005025447 A2 *  3/2005   ............. A61M 1/80
WO   2020159859 A1       8/2020

OTHER PUBLICATIONS

International Search Report and Written Opinion from International Application No. PCT/US2020/017558 mailed Apr. 27, 2020.
(Continued)

*Primary Examiner* — Ariana Zimbouski
*Assistant Examiner* — Eric Rassavong
(74) *Attorney, Agent, or Firm* — Dorsey & Whitney LLP

(57) ABSTRACT

Devices and methods herein remove water from human or animal biological waste fluids using one or more forward osmosis filters. The devices allow for the volume of liquid or semi-liquid waste, including potentially infectious liquid waste, to be filtered to reduce potential exposure of healthcare staff to infectious liquid waste. On a hospital, healthcare staff, or individual patient basis, removing water and concentrating the waste can reduce challenges in management and disposal of the waste. Devices herein use forward osmosis to manage and filter, using one or more suitably sized filter(s), biological fluid exudate from wounds. The devices can be constructed to transport water present in the exudate away from a wound. The wound treatment devices herein not only allow for fluid from wounds to be filtered but also provide structures that can protect wounds from external contaminants, including bacteria and viruses. The wound treatment devices can be incorporated into negative pressure wound therapy systems, if desired.

12 Claims, 5 Drawing Sheets

(51) Int. Cl.
*A61F 13/0206* (2024.01)
*A61F 13/05* (2024.01)
*A61M 1/00* (2006.01)

(52) U.S. Cl.
CPC .......... *A61F 13/0223* (2013.01); *A61F 13/05* (2024.01); *A61M 1/98* (2021.05); *A61M 1/982* (2021.05); *A61F 2013/00876* (2013.01); *A61M 1/60* (2021.05); *A61M 2205/7518* (2013.01); *A61M 2205/7536* (2013.01)

(58) Field of Classification Search
CPC .......... A61F 2013/00876; A61M 1/98; A61M 1/982; A61M 1/60; A61M 2205/7518; A61M 2205/7536; A61M 1/915; A61M 1/69; A61M 2205/75; B01D 61/002; B01D 61/0021; B01D 61/0022; B01D 63/087; B01D 63/089
See application file for complete search history.

(56) References Cited

U.S. PATENT DOCUMENTS

| | | | |
|---|---|---|---|
| 2008/0215020 A1 | 9/2008 | Reeves et al. | |
| 2010/0069829 A1* | 3/2010 | Hutchinson | A61M 1/966 604/35 |
| 2010/0256545 A1* | 10/2010 | Aali | A61F 13/00063 604/304 |
| 2010/0312159 A1* | 12/2010 | Aali | A61F 13/00085 602/44 |
| 2011/0203994 A1 | 8/2011 | Mcginnis et al. | |
| 2012/0316538 A1 | 12/2012 | Heiser et al. | |
| 2014/0243762 A1 | 8/2014 | Aali et al. | |
| 2014/0276488 A1* | 9/2014 | Locke | A61M 1/882 604/319 |
| 2014/0276497 A1 | 9/2014 | Robinson et al. | |
| 2014/0276499 A1* | 9/2014 | Locke | A61M 1/602 604/322 |
| 2015/0174284 A1* | 6/2015 | Payne | B32B 38/0004 604/368 |
| 2015/0342785 A1* | 12/2015 | Payne | B32B 5/02 604/368 |
| 2020/0368410 A1 | 11/2020 | Silver | |
| 2022/0079815 A1 | 3/2022 | Edwards et al. | |

OTHER PUBLICATIONS

U.S. Appl. No. 62/804,759, filed Feb. 13, 2019.
U.S. Appl. No. 62/805,470, filed Feb. 14, 2019.
Advisory Action for U.S. Appl. No. 16/991,669 mailed Aug. 15, 2022.
Final Office Action for U.S. Appl. No. 16/991,669 mailed Apr. 22, 2022.
Issue Notification for U.S. Appl. No. 16/991,669 mailed Aug. 9, 2023.
Notice of Allowance for U.S. Appl. No. 16/991,669 mailed Dec. 13, 2022.
Notice of Allowance for U.S. Appl. No. 16/991,669 mailed Mar. 28, 2023.
International Search Report and Written Opinion from International Application No. PCT/US2021/045551 mailed Nov. 17, 2021.
Non-Final Office Action for U.S. Appl. No. 16/991,669 mailed Dec. 15, 2021.
Wernke, "Glycerol (1,2,3-propanetriol) is a Naturally Occurring Osmotic Agent that Reduces Cerebral Edema and Improves Brian Perfursion", Hunter's Tropical Medicine and Emerging Infectious Disease, 2013, pp. 1-5.
Stout, et al., "Glycerin-Based Hydrogel for Infection Control", Advances in Wound Care, Jan. 9, 2012, pp. 48-51.

* cited by examiner

FORWARD OSMOSIS MEDICAL AND WOUND CARE DEVICES

STATEMENT OF RELATED CASES

This application is a U.S. Nationalization of PCT International Application No. PCT/US2020/017558, filed on 10 Feb. 2020, which relates to and claims priority from U.S. Applications 62/804,759, for "BIOLOGICAL FLUID WATER REMOVAL DEVICE AND METHOD" filed 13 Feb. 2019, and 62/805,470, for "FORWARD OSMOSIS WOUND CARE DEVICE" filed 14 Feb. 2019, the contents of which are incorporated herein by reference in the entirety.

STATEMENT OF GOVERNMENTAL INTEREST

None.

BACKGROUND OF THE DISCLOSURE

Many types of wound care dressings are used to promote healing of the wound and to protect the wound from further harm or contamination. Dressings are available in many materials, constructions, sizes, and shapes. Dressings vary depending on the type and severity and size of the wound, the anatomical location of the wound, the amount of blood and other exudate that needs to be managed, skin conditions, and treatment approach. Wound dressing types can include hydrocolloid, hydrogel, alginate, collagen, foam, transparent, gauze, and non-woven, for example. Additionally, there are various agents, such as antimicrobials or pain relief pharmaceuticals, that may be incorporated into the dressing, if needed or desired.

In combination with specific wound care dressings, negative pressure would therapy (NPWT) can be used to treat hard to heal wounds and has been shown to increase blood flow, reduce edema, enhance wound contraction, and stimulate the formation of granulation tissue. NPWT can be used for various types of wounds such as surgical wounds, open abdominal incisions, dehisced wounds, partial thickness burns, diabetic ulcers, pressure ulcers, flaps and grafts, and traumatic wounds, Traditional NPWT has wound dressings that are used in combination with a cannister for collecting wound exudate as part of the NPWT system. There is at least one disposable NPWT system that is cannister-less and keeps the wound exudate within the wound dressing while a portion of the water in the exudate exits the dressing as water vapor through a water vapor permeable polyurethane film portion of the dressing. This type of disposable NPWT system is smaller, provides for enhanced patient mobility, and is lower cost than traditional NPWT pump systems.

NPWT dressings are typically changed every 2-3 or 3-4 days and depends on the level of exudate, contamination considerations, condition of the dressing, etc. which may result in more frequent changes. Some manufacturers indicate that use may be extended up to 7 days at the clinician's discretion.

Exudate is accumulated fluid in a wound. There are various types of wound exudate including serous exudate which is clear, thin, watery plasma; sanguineous exudate which is fresh bleeding that is seen in deep partial-thickness and full-thickness wounds; serosanguineous exudate which is thin and watery with red blood cells providing a pink tinge; seropurulent exudate which is thin, watery, cloudy, and appears yellow to tan; and purulent exudate which is thick and opaque and appears tan, yellow, green, or brown.

Management of blood and other exudate from the wound is important for wound healing. Excess wetness can damage surrounding tissue, lead to wound infection, be uncomfortable for the patient, and create a strong odor. Ideally the wound is kept moist but not overly moist. Inventive wound dressings can provide alternative approaches beneficial to managing wound exudate and beneficial to wound healing.

There are many biological waste fluids that are disposed of in hospitals, clinics, long term care centers, laboratories, and other healthcare facilities. These fluids are often disposed of in biohazard bags or into the sanitary sewer. Bagged fluid waste needs to be controlled and can be expensive to manage. Having healthcare staff empty biological waste fluids into the sanitary sewer creates the potential for staff exposure to potentially infectious fluids. While there are washing systems available that empty directly to the sanitary sewer system, such as Skyline Medical's Streamway System, they are not available in many settings and are not used to process many of the body fluids that need disposal.

Reduction in the volume of potentially infectious fluids is also useful when there is not a safe location for storage or disposal of the waste, for example where there is no sanitary sewer system immediately available or capability to manage large volumes of bagged liquid waste. Personal care medical devices used for collection of liquid or semi-liquid biological waste also have handling challenges for management and disposal of the waste. Removal of water from these fluids via forward osmosis, on a hospital or healthcare staff or individual patient basis, concentrates the waste and can reduce challenges in management and disposal of the waste.

Forward osmosis is used in a variety of applications including but not limited to concentrating or dewatering foods and beverages; managing industrial wastewater, landfill leachate, and mineral concentration; power generation; controlled delivery of pharmaceuticals; and personal hydration. The fraction of feed material that passes through the membrane is permeate or filtrate while the fraction that is retained by the filter is retentate.

SUMMARY

Forward osmosis wound care devices are set forth. The forward osmosis wound care devices can be of general construction or customized to the specific wound care application and setting. The forward osmosis device is designed to allow water in the fluid exiting the wound to be pulled away from the wound. Fluid transported through the forward osmosis filter to the non-wound side of the forward osmosis layer of the dressing is predominantly water as bacteria, viruses, and most other components do not pass through the filter. The water can then be taken up by an absorbent layer, stored within a liquid storage compartment of the device, or transferred out of the system such as via suction or gravity drainage or evaporation or removal and replacement of the absorbent layer or storage compartment. Filtrate can also be forced out of the wound care device via the positive pressure created as a volume of liquid is osmotically pulled across the forward osmosis filter. While water is removed from the wound exudate, the wound is kept moist.

While many of the same materials and construction approaches of current wound care dressings can be utilized in forward osmosis wound care dressings, forward osmosis wound care dressings have significant advantages. The osmotic wound dressing passively separates water out of the exudate and draws that water away from the wound to an area that is separate and isolated from the wound, on the non-wound side of the forward osmosis filter which is also a bacterial and viral barrier. Advantageously, this reduces the volume of liquid exudate material available for bacterial colonization near the wound area. Additional advantages of moving this volume of liquid to the non-wound side of the filter membrane include that it can increase the time between dressing changes, decrease the number of dressing changes and associated disturbance of the wound, and improve the ability to handle higher flow rates and volumes of exudate. This can result in reduced cost, improved patient comfort, improved patient care, less disruption of the wound healing process, and less contaminated wound dressing waste that needs to be handled by the hospital staff or other caregiver or patient.

For disposable NPWT systems where the wound dressing collects all the exudate instead of collecting the exudate in a cannister, incorporating a forward osmosis system to pull out the water, with or without inclusion of the high moisture vapor transmission film currently used to allow water to exit the NPWT dressing, may allow for handling of certain wounds where currently traditional NPWT is recommended as the system of choice in order to handle higher exudate rates. This can be a significant advantage as disposable NPWT is less costly, less bulky, and more portable than traditional NPWT systems.

As water is pulled from the wound exudate and through the forward osmosis filter, it potentially creates some of the wound healing benefits seen with negative pressure wound therapy. In some cases, flushing the wound with water or saline, preferably sterile, may be beneficial in priming the forward osmosis system. If the forward osmosis dressing and traditional NPWT are used together, there may even be further benefits than with either used alone including but not limited to less frequent dressing changes, less frequent cannister changes, less potentially infectious waste, and less blockage of the vacuum path, for example.

The forward osmosis filter can be used in conjunction with another filtering material that keeps various blood components from potentially clogging or otherwise reducing the efficiency of fluid transfer across the forward osmosis membrane.

Draw materials or draw solutes or osmotic agents, typically salts or sugars or both, are used to draw water from the blood or other exudate and across the filter, leaving potentially infectious agents and other materials behind. This transfer of fluid across the forward osmosis filter reduces the volume of potentially infectious fluids for management and disposal. The solute or solutes can be provided in a multitude of forms including but not limited to crystals, sheets, pills, brine, or impregnated into or onto other substrates such as foam or gauze or gel or other materials or the like.

Glycerin can be used as a draw material and it can be otherwise incorporated into the wound dressing to enhance treatment of the wound. Reference U.S. Pat. No. 4,671,267 Gel-Based Therapy Member and Method.

The forward osmosis device may also contain chemicals or other materials on the filter material or separate from the filter material and on either side or both sides of the filter material to reduce odor, reduce bacterial or viral load, block or bind or transform specific components present in the biological fluid, or absorb left over liquid, for example. Such materials can include but are not limited to activated charcoal, antimicrobials, foam, gauze, sodium polyacrylate, secondary filters, or paper fluff or the like.

The forward osmosis filter material can have different constructions. For example, the forward osmosis filter can be configured of one or more suitable semi-permeable forward osmosis membranes having preselected pore size based on the construction and intended use of the product. Constructions resulting in an overall, small pore size can be used for a wound care dressing, for example. Alternatively, filters with larger pore sizes can also be used in the wound care dressing with resulting greater quantities and larger sizes of components in the exudate able to go through the membrane and greater quantities and larger sizes of draw side materials able to go through the membrane in the opposite direction. Materials and thickness for the membrane and backing layer as well as other factors also impact the functionality of the forward osmosis membrane.

In some applications, movement of the liquid via shaking, vibration, or cross flow along the membrane surface of either or both the draw solution and the exudate may be used to improve performance. The exudate may be combined with sterile water or saline to increase volume and/or decrease viscosity.

The device may also contain manual measurement markers or electronic sensor approaches for monitoring parameters such as total or current fluid output, time markers, concentration of draw solution, pressure, exudate handling capacity available, and other pertinent information. This information as well as associated warning conditions can be recorded by or made available to the healthcare provider, other caregiver, or patient. Collected data can be electronically stored, analyzed, and transmitted.

The wound dressing is secured in place. Depending on the wound type, location, size, and other factors, different approaches to secure the dressing can be used including, but not limited to, adhesive applied on at least one of the dressing layers that has direct access to the skin around the periphery of the wound, using a roller bandage, using a tacky silicone layer, taping the edges, and applying an adhesive bandage over the dressing or the like.

The device may also include various positioning, holding and handling features that simplify placement and use.

In addition to forward osmosis wound care devices, general forward osmosis devices and forward osmosis methods of use for processing biological waste fluids are set forth. The forward osmosis devices can be of general construction or customized to the specific application and biological waste fluid that is being handled. The forward osmosis device is designed to allow the fluid to be readily input into the device, minimizing exposure by the healthcare worker, the patient, or other individual processing the fluid. In at least one embodiment, forward osmosis filter material is incorporated into the biologic waste fluid collection system.

In at least one other embodiment, the forward osmosis membrane is in a device that is not directly incorporated into the biologic waste fluid collection device. Any transfer of the body waste fluid from the patient to the forward osmosis device or from one or more fluid collection or storage devices to the forward osmosis device is designed to minimize potential exposure to the biological waste fluid. The forward osmosis device may also include an outlet to allow the processed fluid to be emptied from the device.

Gravity, peristaltic pumps, suction pumps, and other approaches can be used to transfer the biologic waste fluid into the forward osmosis device as well as transfer the filtrate or permeate out of the forward osmosis device.

Draw materials or draw solutes or osmotic agents, typically salts or sugars or both, are used to draw water from the biological waste fluid and across the filter, leaving potentially infectious agents and other materials behind. This transfer of fluid across the forward osmosis filter reduces the volume of liquid or semi-liquid waste, including potentially infectious fluids, for disposal. The solute or solutes can be provided in a multitude of forms including but not limited to crystals, sheets, pills, brine, or the like, or impregnated into or onto other substrates such as foam or gauze or gel or other materials.

The forward osmosis device may also contain chemicals or other materials on the filter material or separate from the filter material and on either side or both sides of the filter material to reduce odor, reduce bacterial or viral load, block or bind or transform specific components present in the biological waste fluid, or absorb left over liquid, for example. Such materials can include but are not limited to activated charcoal, antimicrobials, foam, gauze, sodium polyacrylate, secondary filters, or paper fluff or the like.

The device may also contain manual measurement markers or electronic sensor approaches for monitoring parameters such as total or current fluid input, total or current fluid output, fluid transferred, time markers, concentration of draw solution, and other pertinent information. This information as well as associated warning conditions can be recorded by or made available to the healthcare provider. For an automated or semi-automated system, measurements can trigger activation of input and output valves or pumps or other devices used to manage the retentate, filtrate, or draw material.

The device may also include various holding and handling features that simplify positioning and maneuvering.

Forward osmosis devices for removing water from biological waste fluids can be part of personal care medical devices used for collection of liquid or semi-liquid biological waste, including but not limited to urological and ostomy devices such as urine leg bags, urostomy bags, ileostomy pouches, etc.

Methods for using the device are for providing for an input of fluid into the system, providing a forward osmosis filter and solute(s) to transfer water from the biological waste fluid side of the filter, and providing for an outlet for removal of the water from the device on the non-biological waste fluid side of the filter.

In some exemplary embodiments, a wound treatment device in accordance with the principles herein can include a filter functioning as a forward osmosis filter to remove water from wound drainage fluid, the filter configured to be connectable to at least one chamber or compartment, the chamber for collecting the processed liquid or permeate; at least one osmotic agent to provide the osmotic potential to pull water from the wound drainage fluid through the forward osmosis filter; the osmotic agent located in the chamber and the osmotic agent in contact with the filter; and the filter and chamber configured to be a wound dressing and configured to be placed over the wound and secured to the patient.

In an exemplary embodiment, the device can include an absorbent layer or a wicking layer or both between the wound and the forward osmosis filter.

In yet another exemplary embodiment the device can include an absorbent layer or a wicking layer or both in the at least one chamber or compartment.

The device can include a wound contact layer positioned between the wound and the forward osmosis filter.

The device can be configured wherein the chamber or compartment can be removed from the filter and replaced.

The device can also be configured wherein the forward osmosis filter and a second layer of material are secured together to form the chamber.

The device can be configured wherein the second layer of material is flexible and can stretch to increase the volume of the chamber.

The device can be configured wherein the second layer of material provides for an increased or high rate of water vapor transmission.

The device can further include a port for access to the chamber to add or remove materials from the chamber.

The device can be configured wherein the wound treatment device is part of a negative pressure wound therapy system.

In accordance with the principles herein, a system for treating and healing wounds can include a forward osmosis wound dressing device configured to cover a wound; the wound dressing device can be configured to transport at least some portion of the water component of the wound fluid exudate away from the wound and out of the wound dressing device via the pressure created by transporting water through a forward osmosis filter; the wound dressing device can be configured to be connectable to a secondary collection compartment that collects the filtrate transported out of the wound dressing device.

The device can be configured wherein at least a portion of the secondary collection compartment material provides for water vapor transmission at an increased or a high rate compared to devices without the secondary collection compartment material.

A negative pressure wound therapy dressing can be constructed in accordance with the principles herein. In an embodiment the wound therapy dressing can have vacuum access for application of vacuum to the wound; the wound dressing can incorporate a forward osmosis membrane to remove water from at least some portion of the wound exudate.

The device can be configured wherein some portion of the exudate is removed and transported away from the dressing via the vacuum for collection into a container.

The device can be configured wherein some portion of the water in the filtrate is removed from the wound dressing via transfer as water vapor through a material with a high moisture vapor transmission rate.

A device for managing wound exudate fluid is set forth. The device can include a secondary collection compartment configured to have a connection point connectable to a wound dressing. The secondary collection compartment can be separated from the wound dressing, if desired. The secondary collection compartment can be configured to store liquid entering the secondary collection compartment via the connection point. The secondary collection compartment can be configured to facilitate a position located near the patient.

The device can be configured wherein at least a portion of the secondary collection compartment material provides for a high rate of water vapor transmission.

An exemplary device for treating biological waste fluids in accordance with the principles herein can include a first chamber for inputting at least one biological waste fluid; a filter functioning as a forward osmosis filter to remove water from the biological waste fluid, the filter configured to be connectable to said first chamber; the forward osmosis filter connectable between the first chamber and a second chamber, the second chamber for collecting the processed liquid or filtrate; at least one draw material to provide the osmotic drive to pull water from the first chamber into the second chamber; the draw material located in the second chamber and the draw material in contact with the filter.

An exemplary system for treating biological waste fluids can include: at least one chamber for receiving one or more biological waste fluids; a filter in contact with a first chamber; draw material connectable to the filter; the filter functioning as a forward osmosis filter to remove water from the biological waste fluid while keeping bacterial and viral contaminants from passing through the filter.

Another exemplary system for treating biological waste fluids can include a forward osmosis filter to convert the waste fluid to reduce the volume of potentially infectious liquid waste and reduce healthcare staff exposure to potentially infectious liquid waste.

The exemplary system can include chemicals or other materials on the filter material or separate from the filter material and on either side or both sides of the filter material to reduce odor, reduce bacterial or viral load, block or bind or transform specific components present in the biological waste fluid, or absorb left over liquid or the like.

Embodiments of methods according to the principles herein can include providing for an opening into a first chamber for input of biological waste fluid into the first chamber; providing a forward osmosis filter in contact with the first chamber; separating the first chamber from a second chamber with the forward osmosis filter; positioning the forward osmosis filter for contact with at least a portion of the biological waste fluids input into the first chamber; and providing for an outlet for removal of filtrate from the second chamber.

DETAILED DESCRIPTION

Figure 1:
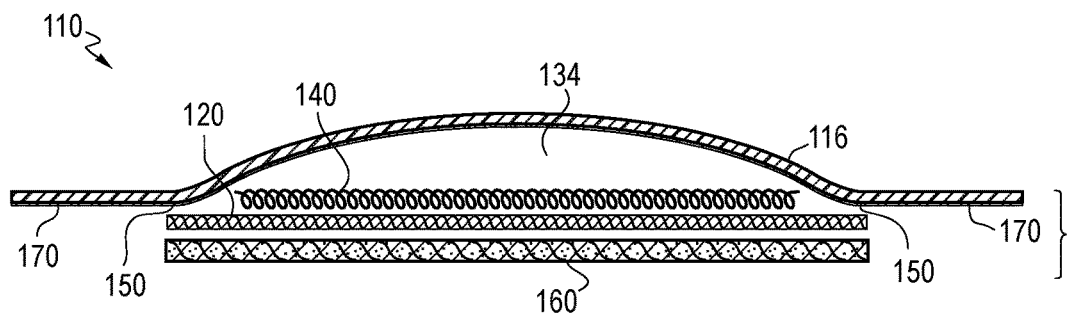
FIG. 1 is a partial cross-sectional drawing of a wound dressing with forward osmosis filter.

FIG. 1 shows a wound dressing 110 with a filter material 120 capable of allowing water to pass through the filter 120 via osmotic pressure while preventing other components, including most of the bacteria and viruses, from passing through. In this embodiment, the wound dressing has at least a forward osmosis filter layer 120 and a second layer 116, which can be a sheet of material, secured to the filter layer 120 at the perimeter 150 to form at least one compartment or chamber 134 between the filter layer 120 and the second layer 116. The second layer 120 is made of a material that does not let liquid or solid materials that are in the chamber to pass through it.

The chamber or chambers 134 include draw solute(s) or draw material(s) 140. Exudate from the wound contacts the forward osmosis filter 120 and a portion of the water in the fluid is pulled through the filter into the chamber(s) 134 by forward osmosis leaving other materials from the exudate on the wound side of the filter including bacteria and viruses. Exudate can be considered biological waste fluid. Biological waste fluid as used herein can include, but is not limited to, wound exudate, blood, urine, digestive fluids, digestive output, sputum, cerebral spinal fluid, lymph and the like once removed from the body and no longer needed.

The second layer 116 extends beyond the seal perimeter 150 and incorporates an adhesive 170 to provide a means for securing the wound dressing 110 to the patient and covering the wound.

The second layer 116 may be optionally made of a material that provides for moisture vapor transmission through it to reduce the amount of liquid contained in the chamber 134. The water vapor transmission rate (MVTR) is comparable with other commonly used wound care dressings, such as those made of single or multilayer thermoplastic polyurethanes. The MVTR for these materials can be adjusted for the specific application. Higher MVTR materials, including higher MVTR polyurethane, are preferred. For example, a polyurethane film with an active area of 10 cm×10 cm and a MVTR of 3000 $g/m^2/24$ hours, would allow a nominal 30 g of water vapor to pass through in 24 hours.

As water vapor leaves the wound dressing through this material, the draw material becomes more concentrated allowing for continued osmotic action. The draw material can pull additional water through the filter membrane which can then pass through the polyurethane film as water vapor and the cycle continues. Preferably, the moisture vapor transmission rate is great enough to keep the chamber 134 from completely filling with water and/or substantially diluting the draw material 140 such that it is no longer effective in pulling water across the membrane 120. At a lower MVTR, chamber 134 may fill up faster. The second layer 116 may be optionally made of stretchable material to allow it to expand and provide for a larger volume inside the chamber 134. This expansion can be measured manually or with electronic sensors to identify the amount of fluid inside the chamber. Alternatively, the second layer 116 can be a rigid or semi rigid material and can be a defined shape, such as a hollow hemisphere. An air vent may be included.

Other items can be added to the wound dressing 110 such as for reducing odor, reducing bacterial or viral load, blocking or binding or transforming specific components present in the biological fluid, adding or changing color, or absorbing liquid or the like.

Additional layers can be added to the wound dressing 110 including, but not limited to, a non-adherent layer (not shown) placed against the wound, an absorbent or wicking layer 160 between the wound and forward osmosis filter, an absorbent or wicking layer between the forward osmosis filter and the second layer (not shown), an oxygen permeable layer to allow oxygen transport to the wound (not shown), and/or a wound filling layer (not shown), for example. For NPWT, a vacuum distribution layer (not shown) may be employed. The vacuum distribution layer may include a more open structure, for example, an open cell foam. Even in non-NPWT wound dressings, this type of open layer may enhance distribution of oxygen to the wound to promote wound healing. One or more of the layers may be multifunctional. Multiple layers can be used for any of the additional layers. The absorbent layers are fluid holding layers and may be hydrophilic or hydrophobic material.

Figure 1A:
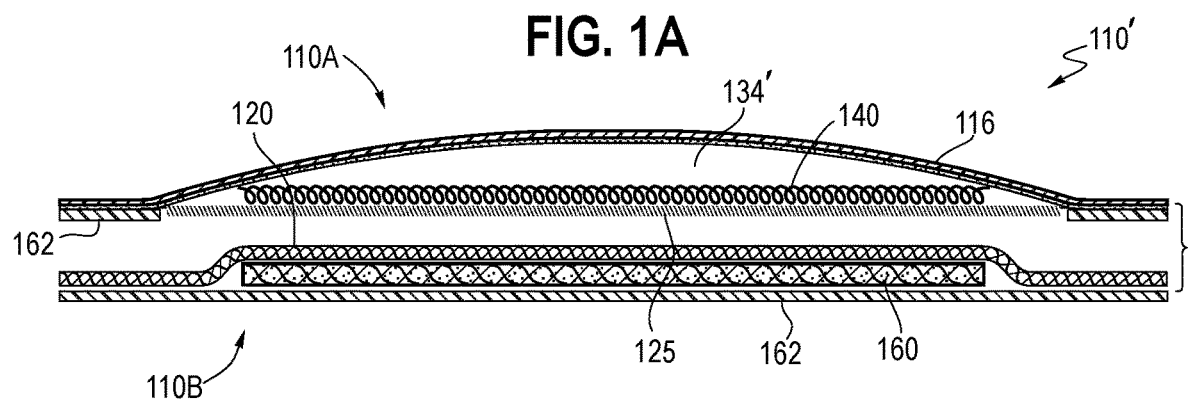
FIG. 1A is an alternate construction of FIG. 1 separating the wound dressing with forward osmosis filter into two sections.

In FIG. 1A, wound dressing 110' comprises section 110A and section 110B. Section 110B is secured to the patient such as with a porous, tacky silicone wound contact and skin adherence layer 162. Section 110B includes forward osmosis filter 120. Section 110A is a removable/replaceable portion of wound dressing 110' in which Chamber 134' is formed between second layer 116 and third layer 125. Removing and changing out section 110A from wound dressing 110' provides for new osmotic agent 140 and new space for filtrate in new chamber 134'. Third layer 125 secures the osmotic materials 140 in place prior to use and allows the osmotic agent to contact the filter 120 during use. The third layer can be, for example, absorbent material that, along with the osmotic agent fills compartment 134'. A portion of the draw material can be imbedded in the absorbent material. The two sections of wound dressing 110', section 110A and section 110B, can be secured together, for example, by using tacky silicone layer 162 along the periphery. As another example, Section 110A can include a gel containing glycerin that acts as both an osmotic agent and water absorbing material. The gel can directly attach to the forward osmosis filter 120.

Figure 2:
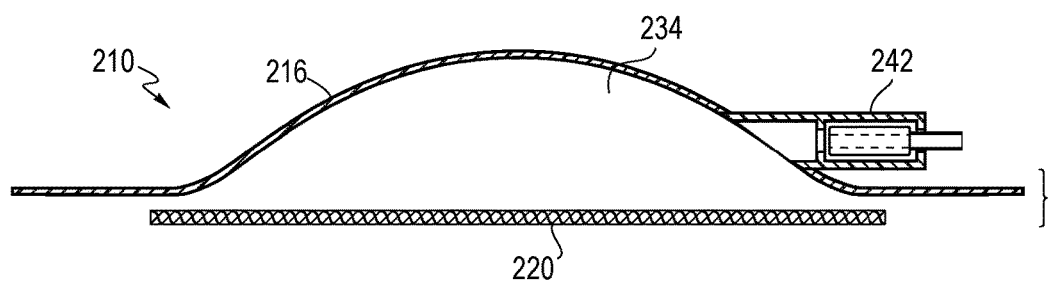
FIG. 2 is a partial cross-section drawing of an access port

In FIG. 2, the wound dressing 210 with forward osmosis filter 220 has at least one access port 242 on second layer 216 for input or removal of material into the chamber or chambers 234. For example, brine can be added into a chamber or chambers 234 through the access port(s) 242. As another example, wound exudate fluid that has gone through the forward osmosis filter 220 into the chamber or chambers 234 and mixed with the draw material can be removed via the port(s) 242. The port 242 can be a syringe port which is normally closed and where the syringe needs to be engaged to open the valve in the port. Other types of ports or access openings can be used. Additionally, the port 242 can be used for access of a sensor to monitor the fluid in the chamber.

Measurement examples include, but are not limited to, fullness of the chamber and salinity. The chamber can be emptied via a vacuum pump, such as a peristaltic pump, attached to the chamber(s) 234. Emptying can be done automatically.

Figure 3:
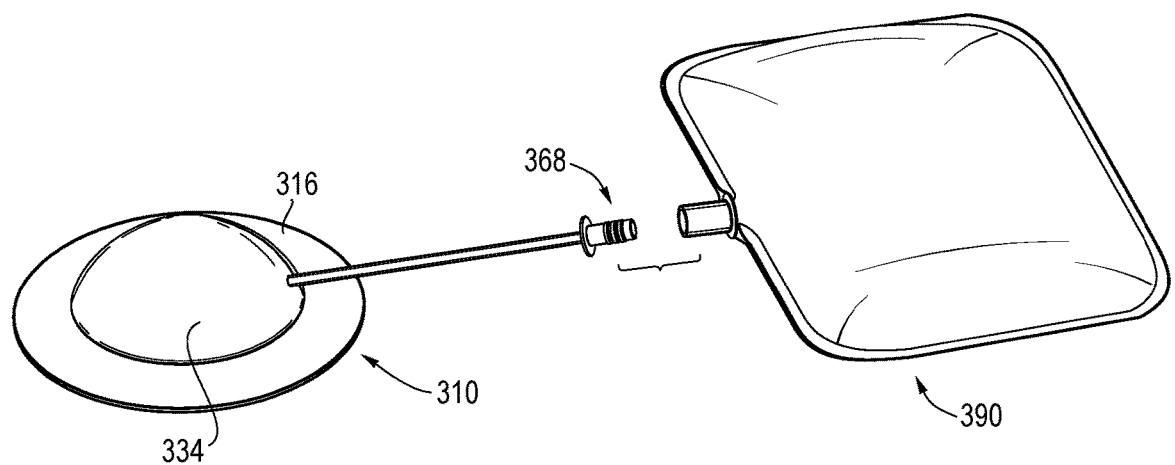
FIG. 3 is a perspective view of a wound dressing with forward osmosis filter and secondary collection compartment.

FIG. 3 shows a forward osmosis filter wound dressing 310 connected to a secondary compartment 390 for collection or management of fluids. The transfer of fluid across the forward osmosis filter creates pressure in chamber 334 and can drive the fluid out of chamber 334 to the secondary collection compartment 390. The system can also be primed by having the draw materials (not shown) extend from the chamber(s) 334 to the secondary compartment 390. Draw materials in the secondary collection compartment 390 can be transferred to the chamber 334. The secondary collection compartment 390 allows for a greater volume of fluid to be collected without necessarily being directly at the wound site. The secondary collection compartment 390 can be optionally removable and replaced, for example if full or uncomfortably heavy for the patient.

As shown in FIG. 2, a valve can be used to open or close access to second chamber 316 of wound dressing 310. A valve can also be used to open or close access to secondary collection compartment 390. The secondary collection compartment 390 can also be made or partially made of materials with a high moisture vapor transmission rate that allows for the fluid volume collected in the compartment to be reduced. Fluid can also be removed from the dressing 310 or the secondary collection compartment 390 via a vacuum pump, peristaltic pump, gravity, or other fluid driver.

The secondary collection compartment 390 can contain one or more absorbent layers or wicking layers (not shown). This secondary collection compartment 390 can be connected to the wound dressing chamber by an extended passageway, such as tubing, allowing for positioning the secondary collection compartment 390 in a location separate from the wound, for example, attached to the patient's belt. Connection 368 allows for opening, removal, or replacement of either wound dressing 310 or secondary collection compartment 390.

The secondary collection compartment 390 may also be useful in wound drainage systems that do not use a forward osmosis filter.

Figure 4:
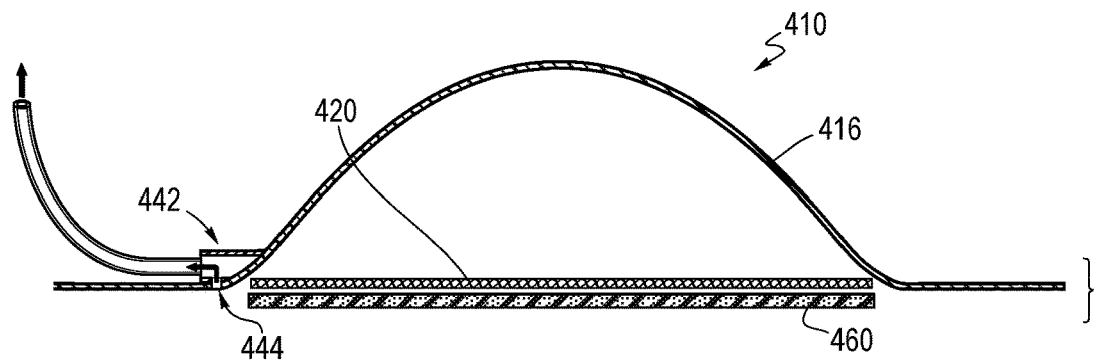
FIG. 4 is a partial cross-sectional drawing of a forward osmosis wound dressing with connected NPWT device

FIG. 4 shows a forward osmosis filter wound dressing 410 in conjunction with a NPWT pump (not shown). The configuration of the wound dressing and location of the pump attachment are constructed to minimize the potential of any exudate from being sucked into the pump tubing or the pump. For example, access opening 444 can be covered with a filter material (not shown) that allows air but not exudate and retentate to pass through it. Other approaches such as creating a long passageway filled with open structure material such as gauze or foam extending from the active portion of the wound dressing to the NPWT adapter 442 and access opening 444 can prevent exudate from going to the pump while still providing a path for application of the vacuum from the NPWT pump.

Vacuum from the NPWT pump is applied to the wound and water in the exudate is pulled through the forward osmosis filter 420 by osmotic agents (not shown) and is captured between the forward osmosis filter 420 and the second layer 416. Other layers and materials can be incorporated as previously described. Foam or gauze 460 are commonly used in filling the wound in traditional NPWT.

Alternatively, forward osmosis can work in combination with a cannister collection system where some exudate can be sucked into the pump tubing. This provides a dual action for managing exudate. This may allow for a small size cannister or other collection device, for example a small bag with foam sealed inside, to be used and may extend the life of the wound dressing.

Figure 5:
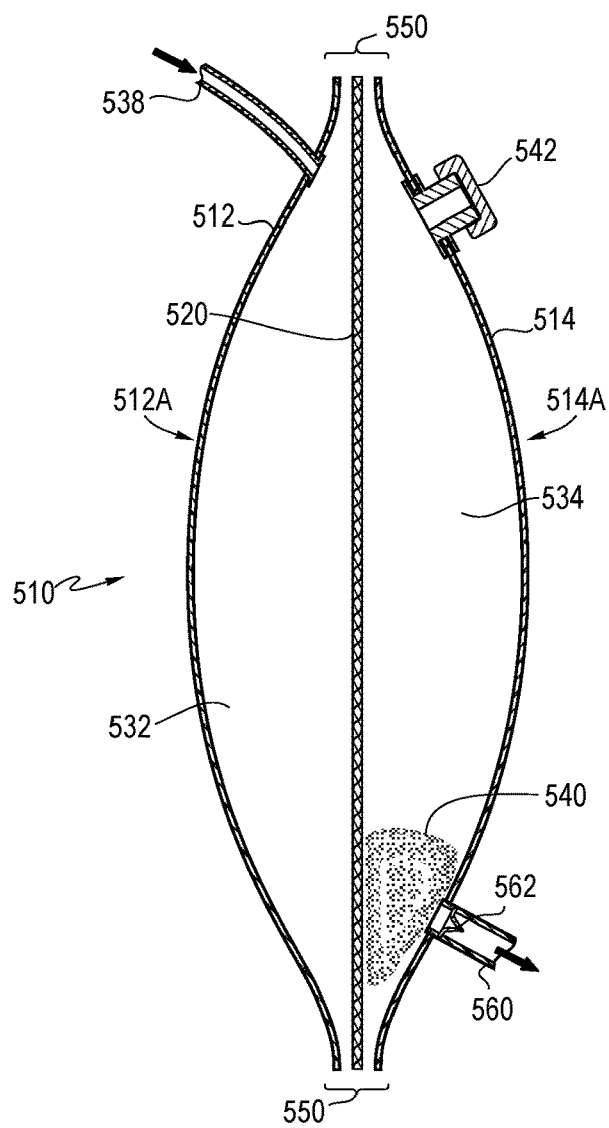
FIG. 5 is a partial cross-sectional drawing of a biological waste fluid collection bag with internal forward osmosis filter.

FIG. 5 shows a fluid collection bag 510 with a filter material 520 capable of allowing water to pass through the filter via osmotic pressure while preventing most of the bacteria and viruses from passing through. In this embodiment, the filter is sealed at the perimeter 550 between the two sheets 512 and 514 of the collection bag 510, thereby creating two separated compartments or chambers 532 and 534. The inlet 538 to the first compartment 532 is located on the first sheet side 512A of the bag and allows the biological waste fluid to enter between the first sheet 512 of the collection bag 510 and the filter 520, preferably directly from the patient. The inlet allows for single, periodic, or continual input of fluid into the first chamber 532.

The outlet 560 from the second compartment 534 is located on the second sheet side 514A of the bag 510 and allows the water that passes through the filter 520 from the first chamber 532 to the second chamber 534 to be emptied from the collection bag 510. The outlet 560 can allow for single, periodic, or continual emptying of the second chamber 534. The outlet 60 in this embodiment has a mechanical valve 562 that preferably allows for one-way flow out of the bag 510. Other mechanical or electromechanical approaches for opening the outlet 560 can be used and can even include automated activation of the valve 562 based on a set volume.

The second chamber includes the draw solute(s) 40 which can be added during or post-manufacture of the device. A separate opening 542 can be included on the second sheet side 514A of the bag 510 to provide access for adding draw material(s) 540. Other items can be added into the chambers of the bag such as for reducing odor, reducing bacterial or viral load, blocking or binding or transforming specific components present in the biological waste fluid, or absorbing left over liquid or the like.

In alternative embodiments (not shown), the container can be a rigid container or a combination of rigid and flexible materials. The container can have multiple inputs. The outlet port can attach to tubing to allow transfer of the water, and other materials in the water, to a selected location for disposal such as a sink or toilet.

As filtrate volume is increased in the second compartment, especially if the compartment is rigid or otherwise constrained, pressure created by the increase in filtrate volume within the compartment can be harnessed to open the outlet valve to expel a portion of the filtrate. In another embodiment (not shown) the inlet port is connected to tubing with a suction cannister port connection on it to allow transfer of collected fluid from the cannister. The tubing can be put into a peristaltic pump to drive the collected fluid from the suction cannister port into the fluid collection bag.

In yet another embodiment (not shown), no outlet is provided or an outlet is created post-manufacture, for example by piercing the container with a spiked connector.

In yet another embodiment (not shown) a forward osmosis device is used for larger volumes or even bulk collections of biological waste fluids, potentially from different sources. It is of larger scale than the forward osmosis device described.

Figure 6:
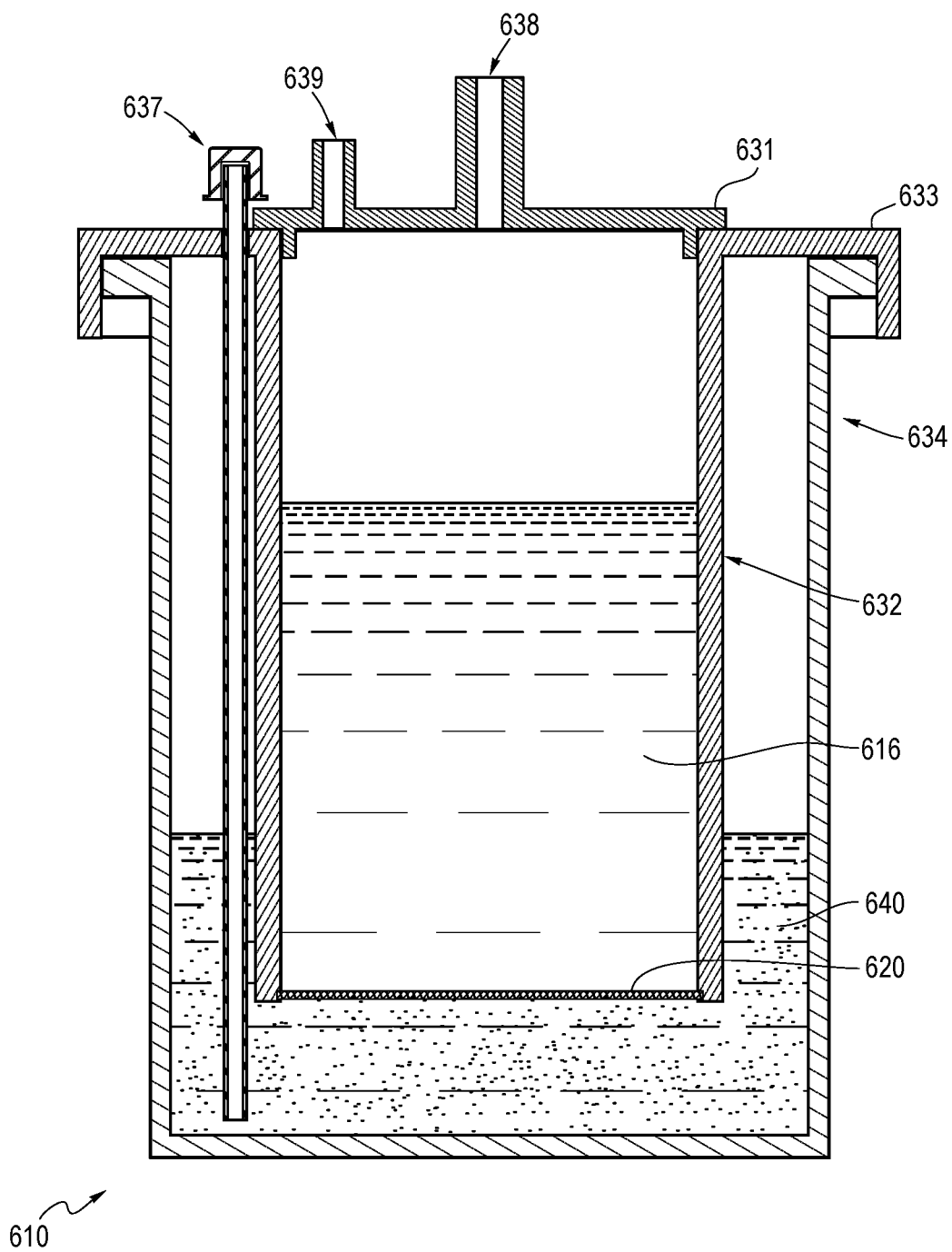
FIG. 6 is a cross-sectional drawing of a suction cannister with integrated forward osmosis filter.

In FIG. 6, the forward osmosis filter 620 is incorporated into a cannister, such as a suction cannister 610. Biological waste fluid 616 enters the receiving chamber 632 of cannister 610 through the inlet port 638 via a vacuum pump connected to vacuum port 639. Alternatively, a peristaltic pump, gravity, or other fluid driver can be used. The forward osmosis filter 620 is secured to the receiving chamber 632. The receiving chamber 632 is inside a second chamber 634 which holds the draw solute(s) 640 and the resulting filtrate. The second chamber 634 never contacts the original biological waste fluid 616 or any resulting retentate from the filtration process. Access port 637 allows for osmotic agent to be added the second chamber 634 and also allows for removal of fluid, which is a combination of filtrate and draw solute(s). Addition or removal of fluids to or from either chamber may be accompanied by air replacement such as by incorporating a filtered air vent (not shown) in the lid(s) 631. and 633. Lid 633 covering a portion of second chamber 634 can be integrated into receiving chamber 632.

A portion of water in the filtrate can be vaporized by adding heat or by other methods to keep the draw solution concentrated. Advantageously, this can reduce the amount of draw material required and associated need for refilling of draw material while reducing the amount of fluid that is otherwise stored and possibly emptied from the second chamber 634.

Figure 7:
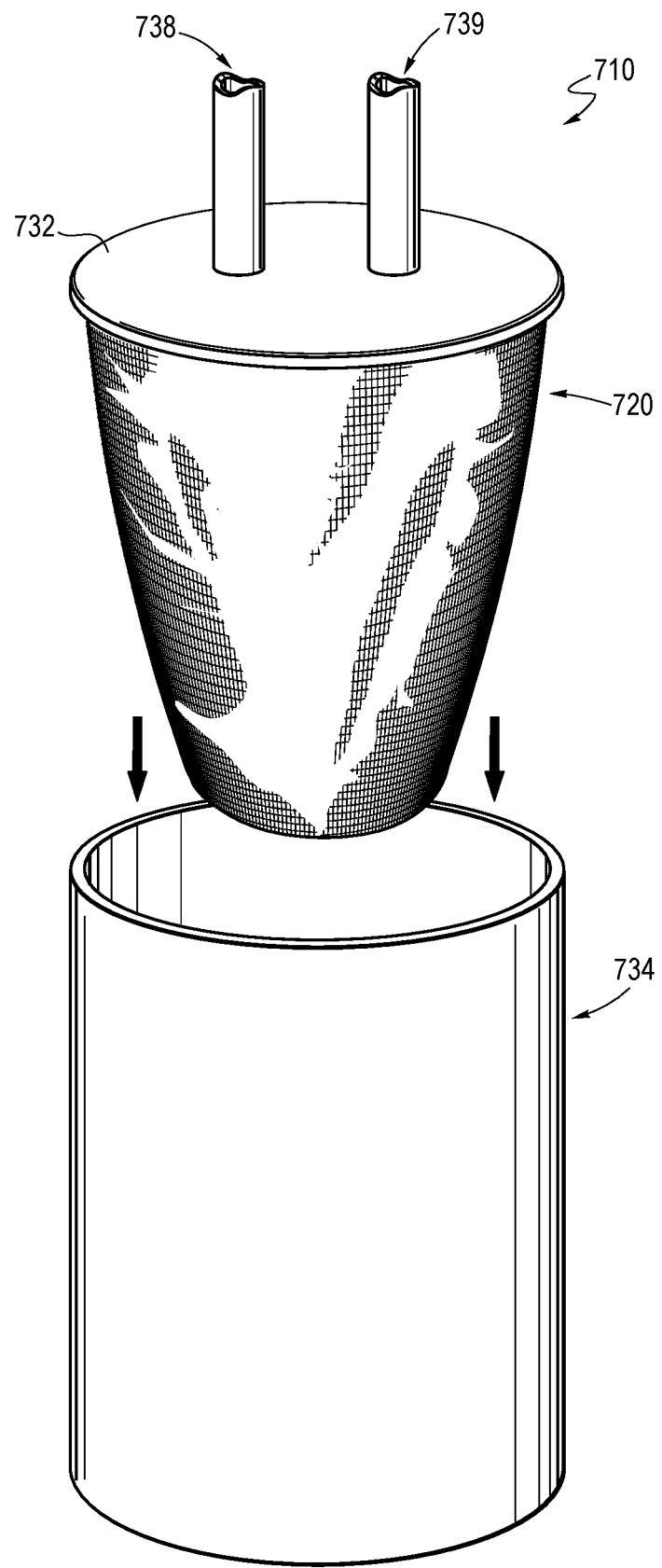
FIG. 7 is a perspective view of a forward osmosis filter bag as part of a suction cannister

FIG. 7 shows a forward osmosis filter bag 710 made from filter material 720 as an alternative configuration of the receiving chamber 632 from FIG. 6. A rigid support (not shown) may be included inside the filter bag if needed to hold the bag open, especially if fluid is being delivered into the bag via suction. Biological waste fluid can be drawn into the system by attaching a vacuum source to vacuum port 739 on lid 732. The biological liquid or semi-liquid waste enters the forward osmosis filter bag 710 via port 738 on lid 732. Draw materials and associated filtrate are in second chamber 734.

While various aspects and exemplary embodiments have been disclosed herein, other aspects and embodiments will be apparent to those skilled in the art. The various aspects and exemplary embodiments disclosed herein are for the purposes of illustration and are not intended to be limiting.

I claim:

1. A wound treatment device, comprising:
a first assembly including a filter configured as a forward osmosis filter to remove water from wound drainage fluid of a wound and a first adherence layer configured to secure the first assembly to a patient with the filter positioned over the wound; and
a second assembly selectively securable and removable from the first assembly, the second assembly including a second layer at least partially defining a chamber for collecting processed liquid or permeate from the filter, a second adherence layer positioned to selectively adhere to the first assembly, and at least one osmotic agent to provide an osmotic potential to pull water from the wound drainage fluid through the forward osmosis filter, the at least one osmotic agent including glycerin, said at least one osmotic agent located in said chamber to be in contact with the filter when the second assembly is secured to the first assembly.

2. The device of claim 1, wherein the first assembly further comprises at least one of an absorbent layer or a wicking layer the forward osmosis filter opposite to the second assembly such that the at least one of the absorbent layer or the wicking layer is positioned to be between the filter and the wound when the first assembly is positioned over the wound.

3. The device of claim 1, wherein the second assembly further comprises at least one of an absorbent layer or a wicking layer in said chamber, the at least one osmotic agent being embedded in the at least one of the absorbent layer or the wicking layer.

4. The device of claim 1, wherein the forward osmosis filter at least partially defines the chamber when the first assembly is secured to the second assembly.

5. The device of claim 4, wherein the second layer provides for a high rate of water vapor transmission that allows for removal of at least some of the water from the chamber as water vapor through the second layer, thereby preventing (1) the chamber from filling with the water beyond a predetermined amount and/or (2) the at least one osmotic agent from being substantially diluted such that the at least one osmotic agent pulls less than a predetermined amount of the water across the forward osmosis filter.

6. The device of claim 1 further comprising:
a port for access to the chamber to add or remove materials from said chamber.

7. The device of claim 1 wherein the wound treatment device is part of a negative pressure wound therapy system.

8. A system for treating and healing wounds comprising:
a wound dressing device including a forward osmosis filter and a chamber configured to cover a wound;
a secondary collection compartment external to the chamber of the wound dressing device and selectively connectable to the wound dressing device, the secondary collection compartment being in fluid communication with the chamber when the secondary collection compartment is connected to the wound dressing device; and
at least one osmotic agent positioned in one or more of the chamber or the second collection compartment;
said wound dressing device configured to transport at least some portion of a water component of a wound fluid exudate of the wound away from the wound and out of the wound dressing device via pressure created by transporting said water through the forward osmosis filter;

wherein the secondary collection compartment collects filtrate transported out of the wound dressing device.

9. The device of claim 8 wherein at least a portion of said secondary collection compartment material provides for a high rate of water vapor transmission.

10. The system of claim 4 further comprising:

chemicals or other materials (1) on the filter or (2) separate from the filter on either side or both sides of the filter, the chemicals or other materials configured to at least one of reduce odor, reduce bacterial or viral load, block or bind or transform specific components present in the biological waste fluid, or absorb left over liquid.

11. The system of claim 8, wherein the one or more osmotic agents extend from the chamber to the secondary collection compartment when secondary collection compartment is connected to the wound dressing device.

12. The system of claim 8, wherein at least some of the one or more osmotic agents are positioned in the secondary collection compartment and transferrable to the chamber when secondary collection compartment is connected to the wound dressing device.

* * * * *